United States Patent
Tanaka et al.

(10) Patent No.: US 8,383,689 B2
(45) Date of Patent: Feb. 26, 2013

(54) SKIN COSMETICS COMPRISING COCOON-SHAPED POLYMER FINE PARTICLES

(75) Inventors: Koichiro Tanaka, Tamba (JP); Shunsaku Tanaka, Tamba (JP); Sadao Negayama, Tamba (JP); Naomi Ishii, Tamba (JP)

(73) Assignee: Aica Kogyo Co., Ltd., Aichi (JP)

( * ) Notice: Subject to any disclaimer, the term of this patent is extended or adjusted under 35 U.S.C. 154(b) by 382 days.

(21) Appl. No.: 12/453,112

(22) Filed: Apr. 29, 2009

(65) Prior Publication Data

US 2010/0278884 A1  Nov. 4, 2010

(51) Int. Cl.
*A61K 47/30* (2006.01)
*A61K 8/02* (2006.01)

(52) U.S. Cl. .................. 514/788.1; 424/401

(58) Field of Classification Search ........... 514/788.1; 424/401
See application file for complete search history.

(56) References Cited

U.S. PATENT DOCUMENTS

| 2009/0061004 A1* | 3/2009 | Birkel et al. ............... 424/489 |
| 2009/0110731 A1* | 4/2009 | Fritz et al. ................. 424/486 |

FOREIGN PATENT DOCUMENTS

| JP | 9-048707 | 2/1997 |
| JP | 2001-206814 | 7/2001 |
| JP | 2003-192538 | 7/2003 |
| JP | 2008-163171 | 7/2008 |
| JP | 2008-273854 | 11/2008 |

OTHER PUBLICATIONS

JP 2008-273854 A, Nov. 13, 2008, machine translation, printed on Jul. 28, 2011.*

* cited by examiner

*Primary Examiner* — Gina C Justice
(74) *Attorney, Agent, or Firm* — Wenderoth, Lind & Ponack, L.L.P.

(57) ABSTRACT

The present skin cosmetics comprising cocoon-shaped polymer fine particles having an average particle size of 1 to 8 μm and cosmetic vehicles show an effect of making fine wrinkles on the skin unnoticeable, letting the skin appear smoother and fairer.

2 Claims, 2 Drawing Sheets

SKIN COSMETICS COMPRISING COCOON-SHAPED POLYMER FINE PARTICLES

TECHNICAL FIELD

The present invention relates to skin cosmetics having an effect of making fine wrinkles on the skin unnoticeable, letting the skin appear smooth and fair.

BACKGROUND ART

Conventionally, various cosmetics, for example makeup cosmetics such as foundation, face powder, rouge and eye shadow, body cosmetics such as body powder and baby powder, and lotions such as pre-shave lotion and body lotion have been proposed as fine particle containing skin cosmetics. These skin cosmetics have been compounded with spherical resin particles such as nylon particles and polymethyl methacrylate particles for the purpose of improving extendability on the skin, improving feel, and making fine wrinkles unnoticeable (Patent Documents 1 to 3). However, these particles are insufficient in their effect of making fine wrinkles on the skin unnoticeable, and there has been demand for fine particles that let the skin appear smoother and fairer.

| [Prior document] | |
| --- | --- |
| Patent Document 1: | JP-A 9-48,707 |
| Patent Document 2: | JP-A 2001-206,814 |
| Patent Document 3: | JP-A 2003-192538 |

SUMMARY OF THE INVENTION

Technical Problem

There are number of wrinkles on the skin. When the skin cosmetics compounded with spherical resin fine particles as described above are rubbed into the skin, not all the spherical fine particles have a shape suitable for filling furrows of wrinkles therewith. That is, the particles settled in furrows are relatively easily released out of the furrows even when sweat is wiped off with a handkerchief for example.

Solution of Problem

The present inventors previously established a method for producing new cocoon-shaped polymer fine particles, and filed it with the Japanese Patent Office as Patent Application No. 2006-353783, and published on Jul. 17, 2008 as Publication No. JP 2008-163171 A1. They also found that the cocoon-shaped polymer fine particles obtained by the above method was quite suitable for the component of the skin cosmetics which could make fine wrinkles on the skin unnoticeable and let the skin appear finer and brighter. They filed the invention of the skin cosmetics with the Japanese Patent Office on Apr. 26, 2007 as Application No. JP 2007-116760 and it was published on Nov. 11, 2008 as Publication No. 2008-273854 A1. Based on these findings, the present inventors have completed the invention.

That is, the present invention relates to:

(1) skin cosmetics comprising cocoon-shaped polymer fine particles having an average particle size of 1 to 8 μm, (2) the skin cosmetics according to (1), wherein the cocoon-shaped polymer fine particles are cross-linked or non-cross-linked polyacrylates, (3) the skin cosmetics according to (1), wherein the content of the cocoon-shaped fine particles in the skin cosmetics is 0.5 to 50% by weight, and (4) the skin cosmetics according to (1), wherein the shape of the cocoon-shaped polymer fine particles is a body of rotation in the form of a capsule-like cylinder having one and the other ends formed respectively into hemispheres or a part thereof, and when a projected figure of the cocoon-shaped fine particle drawn by irradiating the fine particle with light in a direction perpendicular to the side of the cylinder of the fine-particle is superimposed on a basal line B drawn by the following numerical formulas (1) and (2):

$$1.1 \leq L/W \leq 3 \quad (1)$$

$$0.3 \leq R/W \leq 0.6 \quad (2)$$

wherein L is the distance between one and the other ends in rotation axis X of the body of rotation, W is the diameter of the cylindrical rotation body, and R is the radius of the hemisphere, so that the outline P of the projected figure of the cocoon-shaped fine particle will enlarge as large as possible unless it will protrude out of the basal line B, the inside area of the outline B of the projected figure makes up 85% or more of the inside area of the basal line B.

DESCRIPTION OF THE PREFERRED EMBODIMENTS

The cocoon-shaped polymer fine particles used in the present invention are particles in the shape of a body of rotation in the form of a capsule-like cylinder having one end and the other end formed respectively into a hemisphere or a part thereof, and when a projected figure of the cocoon-shaped microparticle drawn by irradiating the fine particle with light in a direction perpendicular to the side of the cylinder of the fine particle is superimposed on a basal line B drawn by the following formulas (1) and (2):

$$1.1 \leq L/W \leq 3 \quad (1) \text{ and}$$

$$0.3 \leq R/W \leq 0.6 \quad (2)$$

wherein L is the distance between one end and the other end in rotation axis X of the body of rotation, W is the diameter of the cylinder, and R is the radius of the hemisphere, so that the outline P of the projected figure of the cocoon-shaped fine particle will enlarge as large as possible unless it will protrude out of the basal line B, the inside area of the outline P of the projected figure makes up 85% or more of the inside area of the basal line B.

The average particle size of the polymer fine particles is usually 1 to 8 μm, preferably 2 to 6 μm.

The average particle size is measured with a precision particle size distribution measuring instrument Multisizer IIE (manufactured by Beckman Coulter, Inc.).

The cocoon-shaped polymer fine particles show special optical diffusivity by their unique shape and the orientation generated by easy rolling in a direction perpendicular to the rotation axis X thereof.

The cocoon-shaped polymer fine particles, when compounded into cosmetics, can make fine wrinkles on the skin more unnoticeable and let the skin appear finer and brighter than by spherical particles.

A method for producing the cocoon-shaped polymer fine particles used in the present invention is described.

A polymerizable monomer mixture containing a polymerizable vinyl monomer and a crosslinkable monomer in an amount of 0.05 to 1% by weight based on the vinyl monomer is subjected to dispersion polymerization to give a dispersion of seed particles, followed by adding, to the dispersion of seed particles, a polymerizable vinyl monomer that is 1 to 5 times larger than the weight of the seed particles and subjecting the mixture to seed polymerization, whereby the cocoon-shaped polymer fine particles can be obtained.

A method of synthesizing the seed particles by using a polymerizable monomer is described.

For synthesizing the seed particles in the present invention from a polymerizable monomer mixture containing a polymerizable vinyl monomer and a crosslinkable monomer, a solvent in which the polymerizable monomer is dissolved but a polymer after polymerization is not dissolved is used. The crosslinkable monomer is added in an amount of usually 0.05 to 1% by weight, preferably 0.1 to 0.6% by weight, more preferably 0.2 to 0.5% by weight, based on the polymerizable vinyl monomer.

When the amount of the crosslinkable monomer added, based on the polymerizable vinyl monomer, is lower than the amount defined above, another polymerizable vinyl monomer to be added later is easily absorbed into the inside of seeds to cause swelling of the seeds, thereby rendering formed particles liable to be spherical. On the other hand, when the amount of the crosslinkable monomer added is higher than the above, aggregation is easily caused during dispersion polymerization, and thus seed particles with even particle size distribution cannot be obtained.

More specifically, a polymerization initiator is dissolved in a solvent and then heated to a temperature suitable for the initiator used, a monomer mixture containing a polymerizable vinyl monomer and a crosslinkable monomer is added thereto, and the mixture is polymerized for 10 to 24 hours under an inert gas stream, for example, a nitrogen gas stream, whereby a dispersion of the objective seed particles can be obtained. On this occasion, various surfactants, or dispersion stabilizers such as polymer protective colloids, may be used to improve the dispersion stability of the polymer particles.

The polymerizable vinyl monomer includes, for example, styrene-based monomers such as styrene, p-methylstyrene, p-chlorostyrene, chloromethylstyrene and α-methylstyrene; acrylate ester-based monomers such as ethyl acrylate, 2-ethylhexyl acrylate, lauryl acrylate, dimethylaminoethyl acrylate and diethylaminoethyl acrylate, methacrylate ester-based monomer such as methyl methacrylate, ethyl methacrylate, lauryl methacrylate, dimethylaminoethyl methacrylate and diethylaminoethyl methacrylate; ethylene glycol mono (meth)acrylate, polyethylene glycol mono(meth)acrylate; alkyl vinyl ethers such as methyl vinyl ether and ethyl vinyl ether; vinyl ester-based monomers such as vinyl acetate and vinyl butyrate; N-alkyl-substituted (meth)acrylamides such as N-methylacrylamide, N-ethylacrylamide, N-methylmethacrylamide, N-ethylmethacrylamide; and nitrile-based monomers such as acrylonitrile and methacrylonitrile. However, usable monomers are not limited to the above-mentioned monomers as long as they are hydrophobic and soluble in an organic solvent.

The cross-linkable monomer includes compounds having 2 or more polymerizable unsaturated bonds in one molecule, for example, aromatic divinyl compounds such as divinyl benzene and divinyl toluene, glycol di(meth)acrylates such as ethylene glycol di(meth)acrylate and diethylene glycol di(meth)acrylate, and tri(meth)acrylates and tetra(meth)acrylates such as trimethylol propane tri(meth)acrylate and pentaerythritol tetra(meth)acrylate. These monomers can be used alone or as a mixture of two or more thereof.

The solvent in which the monomers used in synthesis of seed particles are dissolved but a polymer after polymerization is not dissolved includes, for example, alcohols such as methanol, ethanol, propanol and isopropyl alcohol. The amount of the solvent used is preferably about 3 to 25 times larger than the weight of the monomers.

Examples the dispersion stabilizer that is used include surfactants such as sodium dodecylbenzenesulfonate and sodium laurylsulfate, water-soluble polymers such as gelatin, methyl cellulose, hydroxyethyl cellulose, polyvinyl alcohol, polyvinyl pyrrolidone and polyacrylates, and water-sparingly-soluble inorganic materials such as tricalcium phosphate and magnesium carbonate. These dispersion stabilizers are used alone or in combination of two or more thereof. Polymerization can be conducted preferably with these dispersion stabilizers in an amount used in usual dispersion polymerization.

Examples of the polymerization initiator that is used include organic peroxides such as benzoyl peroxide, o-methoxybenzoyl peroxide, o-chlorobenzoyl peroxide, lauroyl peroxide and cumene hydroperoxide and azo compounds such as 2,2'-azobisisobutyronitrile and 2,2'-azobis-2,4-dimethylvaleronitrile. The amount of the polymerization initiator used is about 0.5 to 5% by weight relative to the monomer mixture.

The synthesized particles are removed by filtration or centrifugation and used in the subsequent step. The average particle size of the seed fine particles is 0.6 to 6 μm, preferably 1.2 to 4.5 μm.

For preparing the cocoon-shaped fine particles from the obtained seed particles, the seed fine particles are dispersed completely in an aqueous medium. For this purpose, the seed fine particles are added to an aqueous medium such as water and dispersed desirably by ultrasonic dispersion, if necessary in the presence of a dispersion stabilizer.

A polymerizable vinyl monomer which is 1 to 5 times (preferably 1.5 to 3.5 times) larger than the weight of the seed fine particles in the aqueous seed particle dispersion, and an oil-soluble initiator, are dissolved and subjected to dispersion with a homomixer or the like or ultrasonic dispersion in an aqueous solution of a surfactant such as sodium lauryl sulfate, to form a monomer emulsion. This monomer dispersion is added to the seed particle dispersion and stirred thereby absorbing the monomer onto the seeds. For improving the solvent tolerance of the polymer fine particles obtained by polymerization reaction, a cross-linkable monomer can be added in an amount of 20% by weight or less, preferably 5 to 15% by weight, based on the polymerizable vinyl monomer, to the monomer emulsion. The conclusion of absorption can be confirmed with an optical microscope or the like. When the amount of the polymerizable monomer relative to the seeds is lower than the above-defined amount, the particles obtained after polymerization are nearly spherical and not preferable. When the amount of the monomer added is higher than the above-defined amount, the particles obtained after polymerization are irregular particles with unevenness, and given the monomer in large excess, become spherical and are not preferable. After it is confirmed that the monomer has been completely absorbed, the reaction mixture is heated and polymerized. At this time, various dispersion stabilizers may be used to improve the dispersion stability of the polymer particles.

In seed polymerization in the present invention, a chain transfer agent, a polymerization inhibitor etc. may be used in suitable amounts in addition to a polymerization initiator.

The polymerization initiator is that which is usually used in this type of reaction. Examples of such polymerization initiator include organic peroxides such as benzoyl peroxide and lauroyl peroxide and azo polymerization initiators such as 2,2'-azobisisobutyronitrile and 2,2'-azobisvarelonitrile. The polymerization initiator is used by dissolving it in the polymerizable monomer. The chain transfer agent may also be one usually used in this type of reaction. Examples of the chain transfer agent that can be preferably used include monothiol, polythiol, xanthogen disulfide, thiuram disulfide, 2-ethylhexyl mercaptoacetate ester, 2-methylmercaptoethyl octanoate ester, methoxybutyl mercaptoacetate ester, methoxybutyl mercaptopropionate ester, α-methylstyrene dimer, and terpirenone. As the polymerization inhibitor, a usually used polymerization initiator such as sodium nitrite, sodium nitrite or cupric chloride is used in a suitable amount.

Polymer fine particles having an average particle size that is 1.3 to 1.5 times larger than the particle size of the seeds used are obtained by subsequent polymerization reaction. Accordingly, the particle size of the polymer fine particles can be regulated in the range of 1 to 8 µm by arbitrarily changing the particle size of the seeds used.

The polymerization temperature in the polymerization reaction in the present invention, though varying depending on the polymerization initiator, the monomers, the polymerization inhibitor added if necessary, the chain transfer agent etc., is usually 30 to 100° C., preferably 50 to 90° C. After polymerization, the polymer fine particles are separated by filtration, washed with water and then dried thereby giving dry powder consisting of cocoon-shaped polymer fine particles.

According to the method described above, cocoon-shaped fine particles shown in electron microscope photographs in FIGS. 1 to 3 are obtained. The fine particles in the photographs contain those which seem spherical, but many of these particles merely seem spherical or elliptical due to the angle at which their photograph was taken, and they are actually cocoon-shaped.

As shown in FIG. 4 and FIG. 5, the shape of the cocoon-shaped polymer fine particles is a body of rotation in the form of a cylinder having one end and the other end formed respectively into a hemisphere or a part thereof, and when a projected figure of the cocoon-shaped fine particle obtained by irradiating the microparticle with light in a direction perpendicular to the side of the cylinder of the microparticle is superimposed on a basal line drawn by the numerical formulas (1) and (2):

$$1.1 \leq L/W \leq 3 \quad (1)$$

$$0.3 \leq R/W \leq 0.6 \quad (2)$$

wherein L is the distance between one end and the other end in rotation axis X of the rotation body, W is the diameter of the rotation body, and R is the radius of the hemisphere, so that the outline P of the projected figure will enlarge as large as possible unless it will protrude from the basal line P, the area within the outline P of the projected plan is 85% or more, preferably 90% or more, of the area within the basal line B.

The basal line B is drawn preferably by the numerical figures (3) and (4):

$$1.2 \leq L/W \leq 2.3 \quad (3)$$

$$0.35 \leq R/W \leq 0.55, \quad (4)$$

and the area within the outline P of the projected figure can be 90% or more of the area within the basal line B.

The polymer fine particles produced by the production method of the present invention have an almost uniform average particle size, and at least 80%, and usually 90%, of the fine particles are cocoon-shaped polymer fine particles.

The content of the spherical composite polymer particles in cosmetics varies depending on the preparation form etc. and is not particularly limited. Usually, the content is 0.1 to 50% by weight, preferably 0.5 to 40% by weight, 1 to 40% by weight for liquid or cream cosmetics, 2 to 40% by weight for solid cosmetics such as a powder. The cocoon-shaped powder fine particles when contained in the above range is superior in an effect of making fine wrinkles etc. on the skin unnoticeable, is excellent in sense of use, and is thus preferable.

Other components than the cocoon-shaped polymer fine particles in the cosmetics of the present invention may be a liquid or solid vehicle for cosmetics and additives mentioned below usually incorporated in cosmetics, as long as the effect of making fine wrinkles on the skin unnoticeable, achieved by optical extendability resulting from the unique shape of the cocoon-shaped polymer fine particles, is not impaired.

As the liquid vehicle, there may be exemplified by a liquid vehicle such as water, hydrous alcohol and oils, solid vehicles such as an extender pigment or solid filler. As the additives, there may be exemplified by fat or oil, higher fatty acids, higher alcohols, sterols, fatty acid esters, metal soup, moisture conditioners, surfactants, polymer substances, thickening agents, colorants, perfumes, preservatives and bactericides, antioxidants, ultraviolet absorbers and special compounding ingredients An oil solution may be one which is used in cosmetics. Examples of the oil solution include hydrocarbon oils such as liquid paraffin, squalane, petrolatum Vaseline and paraffin wax, higher fatty acids such as lauric acid, myristic acid, palmitic acid, stearic acid, oleic acid, behenic acid, undecylenic riacid, oxystearic acid, linolic acid, lanolin fatty acid, and synthetic fatty acids, ester oils such as glyceryl trioctanoate, propylene glycol dicaprate, cetyl 2-ethylhexanoate, and isocetyl stearate, waxes such as beeswax, whale wax, lanolin, carnauba wax, and candelilla wax, fats and oils such as linseed oil, cottonseed oil, caster oil, egg-yolk oil and palm oil, metal soaps such as zinc stearate and zinc laurate, and higher alcohols such as cetyl alcohol, stearyl alcohol, and oleyl alcohol.

Fats, oils, and waxes include, for example, avocado oil, almond oil, olive oil, cacao seed oil, beef tallow, sesame oil, wheat germ oil, safflower oil, shear butter, turtle oil, camellia oil, pasic oil, caster oil, grape oil, macadamia nut oil, mink oil, yolk oil, Japan tallow, palm oil, rose hip oil, hardened oil, silicone oil, orange roughy oil, carnauba wax, candelilla wax, whale wax, jojoba oil, montan wax, beeswax, and lanolin.

Hydrocarbons include, for example, liquid paraffin, petrolatum, paraffin, ceresin, microcrystalline wax, and squalane.

Higher fatty acids include, for example, lauric acid, myristic acid, palmitic acid, stearic acid, oleic acid, behenic acid, undecylenic acid, oxystearic acid, linolic acid, lanolin fatty acid, and synthetic fatty acids.

Higher alcohols include, for example, lauryl alcohol, cetyl alcohol, cetostearyl alcohol, stearyl alcohol, oleyl alcohol, behenyl alcohol, lanolin alcohol, hydrogenated lanolin alcohol, hexyl decanol, octyl decanol, isostearyl alcohol, jojoba alcohol, and decyltetradecanol.

Sterols include, for example, lesterol, dihydroxycholesterol, and phytocholesterol.

Fatty acid esters include, for example, ethyl linoleate, isopropyl myristate, lanolin fatty isopropyl, hexyl laurate, myristyl myristate, cetyl myristate, octyldodecyl myristate, decyl oleate, octyldodecyl oleate, hexyldecyl dimethyloctanoate, cetyl octanoate, cetyl isooctanoate, decyl palmitate, glycerin trimyristate, glycerin tri(capryl caprylate/caprate), propylene glycol dioleate, glycerin triisostearate, glycerin triisooctanoate, cetyl lactate, myristyl lactate and diisostearyl malate, and cyclic alcohol fatty acid esters such as cholesteryl isostearate and cholesteryl 1,2-hydroxystearate.

Metal soaps include, for example, zinc laurate, zinc stearate, magnesium myristate, zinc palmitate, zinc stearate, aluminum stearate, calcium stearate, magnesium stearate, and zinc undecylenate.

Humectants include, for example, glycerin, propylene glycol, 1,3-butylene glycol, polyethylene glycol, sodium dl-pyrrolidonecarboxylate, sodium lactate, sorbitol, sodium hyaluronate, polyglycerin, xylit, and maltitol.

Surfactants include, for example, anionic surfactants such as higher fatty soaps, higher alcohol sulfates, N-acyl glutamate, phosphates, and alkyl sulfates, cationic surfactants such as amines and quaternary ammonium salts, amphoteric surfactants such as those of betaine type, amino acid type, imidazoline type, and lecithin, and nonionic surfactants such as fatty monoglyceride, propylene glycol fatty ester, sorbitan fatty ester, sucrose fatty ester, polyglycerin fatty ester, alkyl alkanolamide, and an ethylene oxide condensate.

Polymer compounds include, for example, natural polymer compounds such as gum arabic, tragacanth gum, guar gum, locust bean gum, karaya gum, iris moss, quince seed, gelatin, shellac, rosin, and casein, semisynthetic polymer compounds such as sodium carboxymethyl cellulose, hydroxyethyl cellulose, methyl cellulose, ethyl cellulose, sodium alginate, ester gum, nitrocellulose, hydroxypropyl cellulose, and crystalline cellulose, and synthetic polymer compounds such as polyvinyl alcohol, polyvinyl pyrrolidone, sodium polyacrylate, carboxyvinyl polymer, polyvinyl methyl ether, polyamide resin, silicone oil, and synthetic resin particles, for example nylon particles, polymethyl methacrylate particles, crosslinked polystyrene particles, silicone particles, urethane particles, and polyethylene particles.

Colorant materials include, for example, inorganic pigments such as iron oxide, ultramarine blue, iron blue pigment, chrome oxide, chrome hydroxide, carbon black, manganese violet, titanium oxide, zinc oxide, talc, kaolin, mica, calcium carbonate, magnesium carbonate, isinglass, aluminum silicate, barium silicate, calcium silicate, magnesium silicate, silica, zeolite, barium sulfate, burning calcium sulfate (plaster), calcium phosphate, hydroxyapatite and ceramic powder, and tar dyes of azo type, nitro type, nitroso type, xanthene type, quinoline type, anthraxquinoline type, indigo type, triphenylmethane type, phthalocyanine type, and pyrene type.

Perfumes include, for example, natural perfumes such as lavender oil, peppermint oil and lime oil, and synthetic perfumes such as ethyl phenyl acetate, geraniol, p-tert-butylcyclohexyl acetate.

Preservatives and bactericides include, for example, methylparaben, ethylparaben, propylparaben, benzalkonium, and benzethonium.

Antioxidants include, for example, dibutyl hydroxy toluene, butyl hydroxy anisole, propyl gallate, and tocopherol.

Ultraviolet absorbers include, for example, inorganic absorbers such as titanium oxide fine particles, zinc oxide fine particles, cerium oxide fine particles, iron oxide fine particles and zirconium oxide fine particles, and organic absorbers such as those of benzoic acid type, p-aminobenzoic acid type, anthranilic acid type, salicylic acid type, cinnamic acid type, benzophenone type, and dibenzoylmethane type.

Special compounding ingredients include, for example, hormones such as estradiol, estrone, ethinyl estradiol, cortisone, hydrocortisone, and prednisone, vitamins such as vitamin A, vitamin B, vitamin C, and vitamin E, skin astringents such as citric acid, tartaric acid, lactic acid, aluminum chloride, aluminum/potassium sulfate, allantoin chlorohydroxy aluminum, zinc p-phenolsulfonate, and zinc sulfate, hair growth promoters such as cantharis tincture, red pepper tincture, ginger tincture, senburi extract, garlic extract, hinokitiol, carpronium chloride, glyceride pentadecanoate, vitamin E, estrogen, and a photosensitive element, and skin-lightening agents such as magnesium phosphate-L-ascorbate and kojic acid.

The present skin cosmetics include solid type such as powder, cakes, semi-solid type such as creams, gels, liquid type such as oil dispersion, aqueous dispersion, water-in-oil emulsion or oil-in water emulsion from formulation aspect, and creams such as after-shaving cream, cleansing cream, cold cream, hand cream, sunscreen cream, lotions such as face lotion and body lotion, foundations, powders such as cake, baby powder, body powder, lip sticks, eye shadow and mascara, perfumes, bath cosmetics from utility aspects.

Preparation for the present skin cosmetics from the cocoon-shaped polymer fine particles and other materials can be conducted according to the conventional methods for preparing cosmetics employing fine solid particles, for example, by mixing the cocoon-shaped polymer particles, a vehicle and other additives at the environment or elevated temperature in an apparatus having a stirrer.

BEST MODE FOR CARRYING OUT THE INVENTION

Hereinafter, the present invention is described in more detail with reference to the Examples, but the present invention is not limited by these examples. In the Examples, the term "parts" refers to parts by weight unless otherwise stated.

Synthesis of Cocoon-Shaped Polymer Fine Particles

Synthesis Example 1

A solution wherein 24 parts of polyvinyl pyrrolidone (molecular weight 360,000) and 6.5 parts of tricaprylylmethyl ammonium chloride (Aliquot 336, Cognis Japan Ltd.) had been dissolved in 840 parts of methanol and 94 parts of ion-exchanged water was heated to 50° C. under stirring in a nitrogen stream. Then, a solution prepared by 2.4 parts of t-butyl peroxypivalate in 100 parts of methyl methacrylate and 0.2 part of ethylene glycol dimethacrylate was added thereto and stirred at the same temperature for 24 hours to give polymer particles (seeds). The average particle size of the particles was 3.34 μm and the standard deviation of their particle size distribution was 7.84%.

0.52 part of surfactant Hightenol NF-13 (polyoxyethylene-alkylether sulfate, Dai-ichi Kogyo Seiyaku Co., Ltd.) and 350 parts of ion-exchanged water were added to 44 parts of the resulting seed particles which were then uniformly dispersed. 280 parts of ion-exchanged water and 1.05 parts of Hightenol NF-13 were mixed with a solution prepared by dissolving 1.4 parts of benzoyl peroxide in a mixture of 63 parts of methyl methacrylate and 7 parts of ethylene glycol dimethacrylate, and then sonicated. The resulting emulsion was added to the above seed particle dispersion and stirred for 30 minutes, thereby absorbing the monomer completely into the seed particles. This dispersion was polymerized at 70° C. for 4 hours in a nitrogen stream to give cocoon-shaped particles having a uniform particle distribution. As a result of measurement of the resulting particles with a precision particle size distribution measuring instrument Multisizer IIE (manufactured by Beckman Coulter, Inc.), the average particle size was 4.38 μm, and the standard deviation of the particle size distribution was 15.4%. An electron microscope photograph of the polymer particles is shown in FIG. 1. As a result of observation with a scanning microscope, the L/W value of the 50 particles was 1.5 to 1.9, and the R/W thereof was 0.41 to 0.55.

Synthesis Example 2

A solution wherein 24 parts of polyvinyl pyrrolidone (molecular weight 360,000) and 5.8 parts of Aliquot 336 (Cognis Japan Ltd.) had been dissolved in 649 parts of methanol and 114 parts of ion-exchange water was heated to 50° C. under stirring in a nitrogen stream. Then, a solution prepared by 1.2 parts of 2,2'-azobisisobutyronitrile in 79.8 parts of methyl methacrylate and 0.4 part of ethylene glycol dimethacrylate was added thereto and stirred at the same temperature for 24 hours to give polymer particles. The average particle size of the particles was 2.50 μm and the standard deviation of their particle size distribution was 20.8%.

0.52 part of Hightenol NF-13 (Dai-ichi Kogyo Seiyaku Co., Ltd.) and 350 parts of ion-exchange water were added to 35 parts of the resulting seed particles which were then uniformly dispersed. 280 parts of ion-exchange water and 1.05 parts of Hightenol F-13 were mixed with a solution prepared by dissolving 1.05 parts of benzoyl peroxide in a mixture of 63 parts of methyl methacrylate and 7 parts of ethylene glycol dimethacrylate, and then sonicated. The resulting emulsion was added to the above seed particle dispersion and stirred for 30 minutes, thereby absorbing the monomer completely into the seed particles. 0.14 part of sodium nitrite was added to this dispersion which was then polymerized at 70° C. for 4 hours in a nitrogen stream to give cocoon-shaped particles having a uniform particle distribution. The average particle size of the resulting particles was 3.58 μm, and the standard deviation of the particle size distribution was 19.3%. It was observed under a scanning microscope that among the 50 particles, there were 3 particles that did not satisfy $1.1 \leq L/W \leq 3.0$ and $0.3 \leq R/W \leq 0.6$, and the L/W value of the other particles was 1.2 to 1.4, and the R/W thereof was 0.35 to 0.52.

An electron microscope photograph of the polymer particles is shown in FIG. 2.

Synthesis Example 3

0.5 part of surfactant Prisurf A210G (Dai-ichi Kogyo Seiyaku Co., Ltd.) and 350 parts of ion-exchange water were added to 35 parts of seed particles obtained in the same manner as in Example 2, and the mixture was uniformly dispersed. 280 parts of ion-exchange water and 1.5 parts of Prisurf A210G were mixed with a solution prepared by dissolving 1.05 parts of benzoyl peroxide in 70 parts of methyl methacrylate, and then sonicated. The resulting emulsion was added to the above seed particle dispersion and stirred for 30 minutes, thereby absorbing the monomer completely into the seed particles. 0.14 part of sodium nitrite and 15 parts of 10% aqueous solution of polyvinyl alcohol (GH-17, manufactured by Nippon Synthetic Chemical Industry Co., Ltd.) were added to this dispersion which was then polymerized at 70° C. for 4 hours in a nitrogen stream to give cocoon-shaped particles having a uniform particle distribution. The average particle size of the resulting particles was 3.82 μm, and the standard deviation of the particle size distribution was 20.1%. It was observed under a scanning microscope that among the 50 particles, there were 3 particles that did not satisfy $1.1 \leq L/W \leq 3$ and $0.3 \leq R/W \leq 0.6$, and the L/W value of the other particles was 1.2 to 1.45, and the R/W thereof was 0.43 to 0.55.

Synthesis Example 4

The same operation as described above was conducted except that 70.0 parts of the seed particles obtained in Synthesis Example 2 were used. The resulting fine particles were spherical fine particles having an average particle size of 2.78 μm.

Example 1

| Oily compact foundation | |
| --- | --- |
| Carnauba wax | 4.0 parts |
| Solid paraffin | 4.0 parts |
| Cetanol | 4.0 parts |
| Lanolin | 7.0 parts |
| Liquid paraffin | 6.0 parts |
| Behenyl alcohol | 4.0 parts |
| Titanium oxide | 13.0 parts |
| Iron oxide | 10.0 parts |
| Cocoon-shaped polymer fine particles (Synthesis Example 1, particle size 4.4 μm) | 40.0 parts |
| Sericite | 8.0 parts |

From the above composition, an oily compact foundation was produced.

Example 2

| Powder | |
| --- | --- |
| Cocoon-shaped polymer fine particles (Synthesis Example 1) | 12.0 parts |
| Solid paraffin | 5.0 parts |
| Petrolatum | 14.0 parts |
| Liquid paraffin | 40.0 part |
| Glycerin monostearate | 2.0 parts |
| Polyoxyethylene sorbitan monooleate ester | 2.0 parts |
| Purified water | 24.7 parts |
| Soap powder | 0.1 part |
| Borax | 0.2 part |

From the above composition, powder was produced.

Example 3

| Lotion | |
| --- | --- |
| Oil phase | |
| Stearic acid | 2.0 parts |
| Cetyl alcohol | 1.2 parts |
| Vaseline | 5.0 parts |
| Liquid paraffin | 1.0 part |
| Polyoxyethylene oleyl ether (20 E.O.) | 3.0 parts |
| Polyoxyethylene sorbitan monolaurate (4 E.O.) | 3.0 parts |
| Aqueous phase | |
| Propylene glycol | 4.0 parts |
| Triethanolamine | 1.0 part |
| Purified water | 64.6 parts |
| Cocoon-shaped fine particles (Synthesis Example 1) | 5.0 parts |
| Titanium oxide | 0.2 part |

From the above composition, a lotion was produced.

Comparative Example 1

An oily compact foundation was prepared using the same composition as in Example 1 except that the cocoon-shaped fine particles in Synthesis Example 4 were used.

Comparative Example 2

Powder was prepared using the same composition as in Example 2 except that the cocoon-shaped fine particles in Synthesis Example 4 were used.

Comparative Example 3

A lotion was prepared using the same composition as in Example 3 except that the cocoon-shaped fine particles in Synthesis Example 4 were used.

Experimental Example 4

When the respective cosmetics were used to do a makeup, a panel of 20 persons evaluated, under the following criteria, whether fine wrinkles etc. were made unnoticeable or not, and whether the makeup was done with natural finish or not
Evaluation Criteria
⊚: 16 or more persons evaluated that the products were improved as compared with those in the Comparative Examples.
○: 11 to 15 persons evaluated that the products were improved as compared with those in the Comparative Examples.
Δ: 6 to 10 persons evaluated that the products were improved as compared with those in the Comparative Examples.
x: 5 or less persons evaluated that the products were improved as compared with those in the Comparative Examples.
The results are shown in Table 1.

TABLE 1

|  | Oily compact foundation in Example 4 | Powder in Example 5 | Lotion in Example 6 |
|---|---|---|---|
| Object of comparison | Comparative Examples 1 | Comparative Examples 2 | Comparative Examples 3 |
| Degree of unnoticeable fine wrinkles | ⊚ | ⊚ | ⊚ |
| Natural finish | ⊚ | ○ | ○ |

As shown above, the skin cosmetics compounded with the cocoon-shaped resin fine particles of the present invention, as compared with the skin cosmetics compounded with spherical resin fine particles, made fine wrinkles unnoticeable and gave natural finishing effect.

[Description of Symbols]

Figure 1:
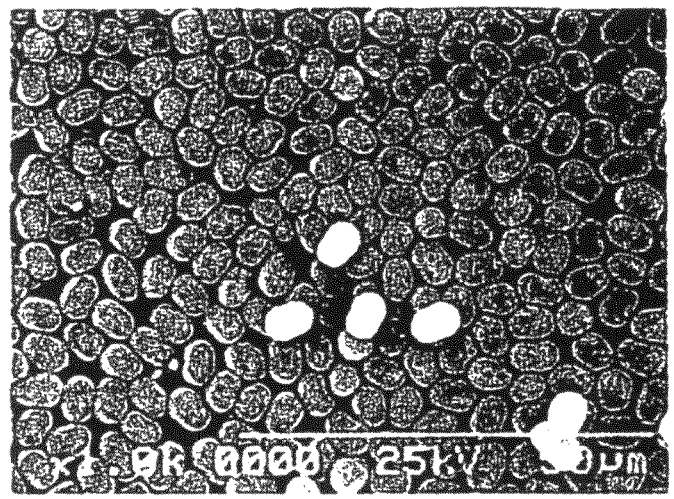
FIG. 1 is a photomicrograph of cocoon-shaped polymer fine particles obtained in Synthesis Example 1.
Figure 2:
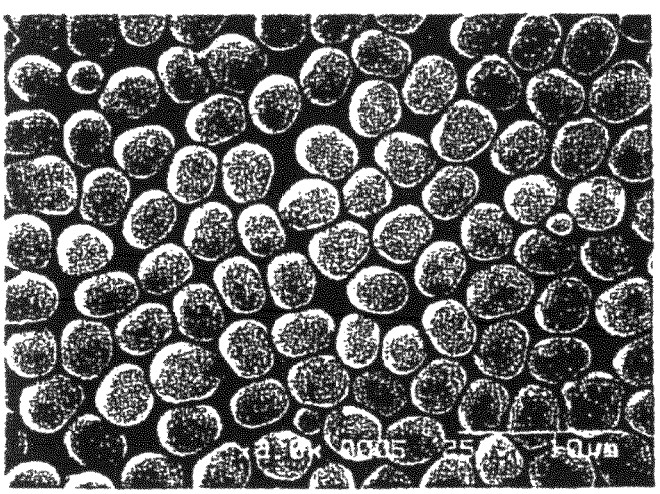
FIG. 2 is a photomicrograph of cocoon-shaped polymer fine particles obtained in Synthesis Example 2.
Figure 3:
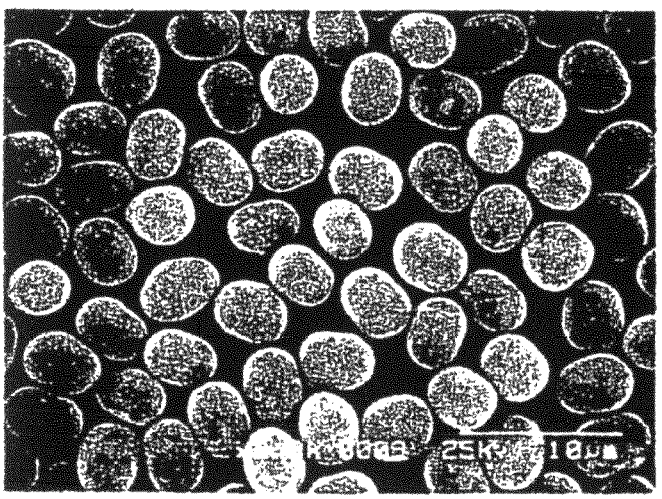
FIG. 3 is a photomicrograph of cocoon-shaped polymer fine particles obtained in Synthesis Example 3.
Figure 4:
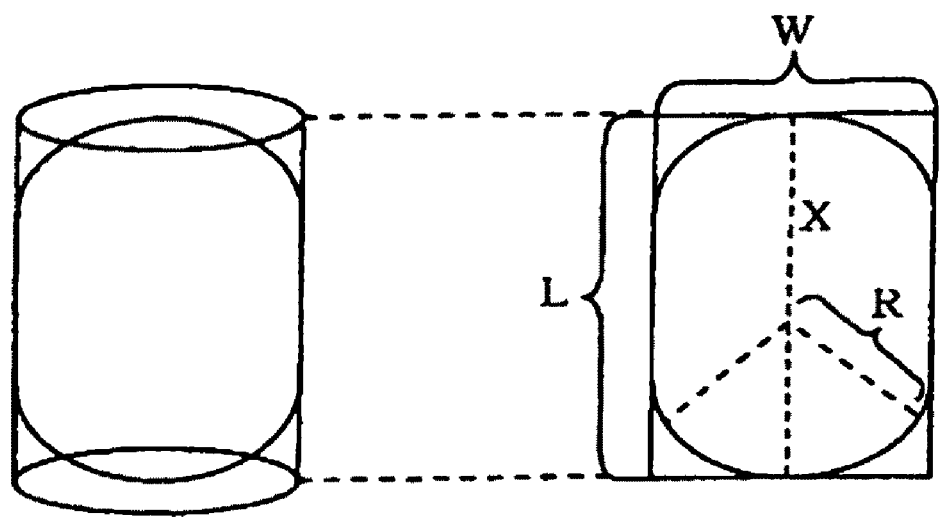
FIG. 4 is a schematic diagram of the cocoon-shaped polymer fine particles of the present invention.
Figure 5:
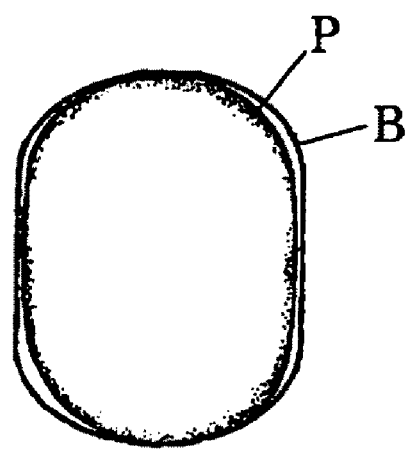
FIG. 5 is a schematic diagram of superimposed basal line B and outline P of the projected figure of a cocoon-shape fine particle.

L: Distance between one and the other ends in rotation axis X of the rotation body of the cocoon-shaped fine particles
W: Diameter of the cylinder of a cocoon-shaped body
R: Radius of hemisphere
X: Rotation axis of cocoon-shaped body
B: Basal line drawn by the numerical formulas (1) and (2)
P: Outline of the projected figure of the cocoon shape fine particle drawn by irradiating the fine particle with light in a direction perpendicular to the side of the cylinder of the fine-particle

INDUSTRIAL APPLICABILITY

The present skin cosmetics comprising cocoon-shaped polymer fine particles having an average particle size of 1 to 8 μm and cosmetic vehicles has good extendability on the face skin and show an effect of making fine wrinkles on the skin unnoticeable, letting the skin appear smooth and fair

The invention claimed is:

1. A method for applying a skin cosmetic on skin, which comprises:
   providing a skin cosmetic comprising:
   (a) cocoon-shaped polymer fine particles having an average particle size of 1 to 8 μm,
   wherein the shape of the cocoon-shaped polymer fine particles is a rotation body in the form of a capsule-like cylinder having one end and the other end formed respectively into a hemisphere or a part thereof, and when a projected figure of the cocoon-shaped fine particle drawn by irradiating the fine particle with light in a direction perpendicular to the side of the cylinder of the fine-particle is superimposed on a basal line B drawn by the following numerical formulas (1) and (2):

$$1.1 \leq L/W \leq 3 \quad (1)$$

$$0.3 \leq R/W \leq 0.6 \quad (2)$$

wherein L is the distance between one end and the other end in rotation axis X of the rotation body, W is the diameter of the cylinder of the rotation body and R is the radius of the hemisphere, so that the outline P of the projected figure of the cocoon-shaped fine particle will enlarge as large as possible unless it will protrude out of the basal line B, the inside area of the outline P of the projected figure makes up 85% or more of the inside area of the basal line B,
   with
   (b) a cosmetic vehicle and
   (c) other additives for a skin cosmetic, and
   applying the skin cosmetic on skin.

2. The method according to claim 1, wherein the content of (a) the cocoon-shaped polymer fine particles is
   0.1 to 50% by weight of the cosmetic when the cosmetic is a liquid or cream type, or
   2 to 40% by weight of the cosmetic when the cosmetic is a solid type.

* * * * *